United States Patent
Dupuis (12)

(10) Patent No.: US 6,294,158 B1
(45) Date of Patent: *Sep. 25, 2001

(54) COSMETIC COMPOSITION CONTAINING AN ANIONIC POLYMER AND AN ACRYLIC TERPOLYMER, AND USE OF THIS COMPOSITION FOR THE TREATMENT OF KERATINOUS MATERIAL

(75) Inventor: Christine Dupuis, Paris (FR)

(73) Assignee: L'Oreal, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/332,005

(22) Filed: Jun. 14, 1999

(30) Foreign Application Priority Data

Jun. 15, 1998 (FR) .................................................. 98 07514

(51) Int. Cl.$^7$ ............................... A61K 7/06; A61K 7/11; A61K 7/00
(52) U.S. Cl. ................. 424/70.1; 424/70.16; 424/70.22; 424/401
(58) Field of Search ............................... 424/70.16, 401, 424/70.1, 70.11, 70.12, 70.22, 70.15, 59

(56) References Cited

U.S. PATENT DOCUMENTS

| 5,015,711 | 5/1991 | Simonet et al. ..................... 526/301 |
| 5,066,710 | 11/1991 | Simonet et al. ..................... 524/555 |
| 5,294,693 | 3/1994 | Egraz et al. ......................... 526/310 |
| 5,362,415 | 11/1994 | Egraz et al. ................... 252/174.24 |
| 5,637,306 | 6/1997 | Cauwet et al. ....................... 424/401 |
| 6,060,041 | * 5/2000 | Candau et al. . |
| 6,214,326 | * 4/2001 | Dupuis ................................ 424/70.1 |

FOREIGN PATENT DOCUMENTS

| 0350414 | 1/1990 | (EP) . |
| 0577526 | 1/1994 | (EP) . |
| 0824914 | 2/1998 | (EP) . |
| WO93/24544 | 12/1993 | (WO) . |

* cited by examiner

Primary Examiner—Diana Dudash
Assistant Examiner—Gina Yu
(74) Attorney, Agent, or Firm—Jacobson Holman, PLLC

(57) ABSTRACT

The present application relates to cosmetic compositions containing, in a cosmetically acceptable aqueous medium, at least one anionic polymer and an acrylic terpolymer, as well as to the use of these compositions for treating keratinous material.

The acrylic terpolymer comprises:
  a) about 20 to 70% by weight of a carboxylic acid containing $\alpha,\beta$-monoethylenic unsaturation;
  b) about 20 to 80% by weight of a non-surfactant monomer containing monoethylenic unsaturation, which is different from a), and
  c) about 0.5 to 60% by weight of a nonionic urethane monomer which is the product of reaction of a monohydric nonionic surfactant with a monoisocyanate containing monoethylenic unsaturation.

The invention relates in particular to leave-in hair products, such as gels, mousses, lacquers and sun compositions.

33 Claims, No Drawings

COSMETIC COMPOSITION CONTAINING AN ANIONIC POLYMER AND AN ACRYLIC TERPOLYMER, AND USE OF THIS COMPOSITION FOR THE TREATMENT OF KERATINOUS MATERIAL

The present invention relates to cosmetic compositions containing, in combination, at least one anionic polymer and an acrylic terpolymer, as well as to the use of these compositions for the treatment of keratinous material, in particular the skin and the hair.

Anionic polymers are generally used for their fixing properties, in particular for formulating styling and fixing hair gels.

It is advantageous to formulate, for haircare and hairstyling, hair compositions containing anionic polymers, which have a high viscosity and are in a thick gel form which spreads well.

For this, use is generally made of thickening and/or gelling polymers. However, the introduction of anionic polymers into thickeners often leads to problems of fluidization and of loss of clarity of the support, and cosmetic performance levels obtained are sometimes insufficient for care and styling products.

Thickening and/or gelling polymers are known which contain in their chain a hydrophilic part and a hydrophobic part consisting of a fatty chain, such as the product "Pemulen TR1" sold by the company Goodrich or the "Acrysol" polymers sold by the company Rohm & Haas. The polymer "Pemulen TR1", used in combination with anionic polymers, does not lead to a gel of satisfactory texture or transparency and does not give satisfactory cosmetic results, in particular as regards the fixing power, the ease of disentangling, the softness and the feel. The polymer "Acrysol 44", used in combination with an anionic polymer, leads to a fluid and cloudy gel.

The Applicant has discovered, surprisingly, that by using a novel family of thickening and/or gelling polymers and by combining them with anionic polymers, it is possible to obtain cosmetic formulations which have a satisfactory viscosity at a relatively low pH, which are not pasty or greasy, which spread well on the skin and the hair and which give the hair good properties of softness, feel and easy disentangling while at the same time having good styling and/or fixing properties.

The subject of the present invention is thus cosmetic compositions for the treatment of keratinous material containing, in a cosmetically acceptable aqueous support, at least one anionic polymer and an acrylic terpolymer which will be defined in greater detail later in the description.

This polymer makes it possible in particular to prepare leave-in or rinse-out, aqueous-organic or aqueous compositions containing cosmetically acceptable solvents, ranging from gelled products to sticks or solid tubes.

The advantages of this terpolymer are that it is stable in electrolytic medium and has very good thickening power at a pH equal to or above 5.5, making it possible to achieve a good level of viscosity and to be able to use high concentrations of alcohol.

The acrylic terpolymer used in accordance with the invention is soluble or swellable in alkalis. It is characterized in that it comprises:

a) about 20 to 70% by weight, preferably 25 to 55% by weight, of a carboxylic acid containing $\alpha,\beta$-monoethylenic unsaturation;

b) about 20 to 80% by weight, preferably 30 to 65% by weight, of a non-surfactant monomer containing monoethylenic unsaturation, which is different from a), and c) about 0.5 to 60% by weight, preferably 10 to 50% by weight, of a nonionic urethane monomer which is the product of reaction of a monohydric nonionic surfactant with a monoisocyanate containing mono-ethylenic unsaturation.

The carboxylic acid containing $\alpha$, $\beta$-mono-ethylenic unsaturation a) can be chosen from many acids and in particular acrylic acid, methacrylic acid, itaconic acid and maleic acid. Methacrylic acid is preferred. A large proportion of acid is essential in order to give a polymer structure which dissolves and gives a thickening effect by reaction with an alkaline compound such as sodium hydroxide, alkanolamines, aminomethylpropanol or aminomethylpropanediol.

The terpolymer should also contain a large proportion, indicated above, of a monomer b) containing monoethylenic unsaturation which has no surfactant properties. The preferred monomers are those which give polymers that are water-insoluble when they are homopolymerized and are illustrated by $C_1$–$C_4$ alkyl acrylates and methacrylates such as methyl acrylate, ethyl acrylate and butyl acrylate, or corresponding methacrylates. The monomers more particularly preferred are methyl and ethyl acrylates. Other monomers which can be used are styrene, vinyltoluene, vinyl acetate, acrylonitrile and vinylidene chloride. Non-reactive monomers are preferred, such monomers being those in which the single ethylenic group is the only group which is reactive under the polymerization conditions. However, monomers which contain groups that are reactive under the action of heat can be used in certain situations, such as hydroxyethyl acrylate.

The monohydric nonionic surfactants used to obtain the nonionic urethane monomer c) are well known and are generally alkoxylated hydrophobic compounds containing an alkylene oxide forming the hydrophilic part of the molecule. The hydrophobes generally consist of an aliphatic alcohol or an alkylphenol in which a carbon chain containing at least six carbon atoms constitutes the hydrophobic part of the surfactant.

The preferred monohydric nonionic surfactants have the formula:

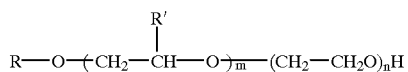

in which R is a $C_6$–$C_{30}$ alkyl or $C_8$–$C_{30}$ aralkyl group, R' is a $C_1$–$C_4$ alkyl group, n is an average number ranging approximately from 5 to 150 and m is an average number ranging approximately from 0 to 50, with the condition that n is at least as large as m and that n+m=5–150.

As preferred $C_6$–$C_{30}$ alkyl groups, mention may be made of dodecyl and $C_{18}$–$C_{26}$ alkyl radicals. As aralkyl groups, mention may be made more particularly of ($C_8$–$C_{13}$) alkylphenyl groups. The preferred group R' is the methyl group.

The monoisocyanate containing monoethylenic unsaturation which is used to form the nonionic urethane monomer c) can be chosen from a wide variety of compounds. A compound containing any copolymerizable unsaturation such as acrylic or methacrylic unsaturation can be used. An allylic unsaturation imparted by allyl alcohol can also be used. The preferred monoethylenic monoisocyanate is $\alpha,\alpha$-dimethyl-m-isopropenylbenzyl isocyanate.

The acrylic terpolymer defined above is obtained by aqueous emulsion copolymerization of the components a), b) and c) which is entirely common and described in patent application EP-A-0,173,109.

As terpolymers which can be used according to the invention, mention may be made of the products of reaction of methacrylic acid as component a), of ethyl acrylate as component b) and of a nonionic urethane macromonomer as component c), having the following structure:

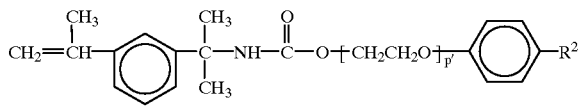

in which p' ranges from 6 to 150 and is preferably equal to 30 and $R^2$ is a $C_8$–$C_{13}$ alkyl radical, such as that described in Example 3 of patent application EP-A-0,173,109.

The preferred acrylic terpolymer used according to the invention is obtained from methacrylic acid as component a), methyl acrylate as component b) and a nonionic urethdne macromonomer as component c), having the following structure:

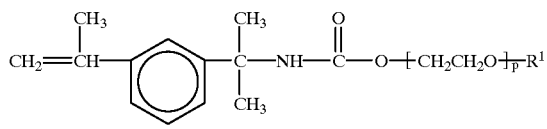

in which p ranges from 6 to 150 and $R^1$ is a $C_{18}$–$C_{26}$ alkyl radical, preferably $C_{20}$–$C_{24}$ linear, of plant origin, such as the docosyl radical.

The acrylic terpolymer is present in the cosmetic compositions of the invention in concentrations ranging from 0.01 to 20% by weight relative to the total weight of the composition, and preferably from 0.1 to 10% by weight.

According to the invention, any anionic polymer known per se can be used. Needless to say, one or more anionic polymers can be used.

Thus, the anionic polymers generally used are polymers containing groups derived from carboxylic, sulphonic or phosphoric acid and have a molecular weight of between about 500 and 5,000,000.

The carboxylic groups are provided by unsaturated mono- or dicarboxylic acid monomers such as those corresponding to the formula:

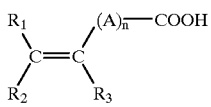

(I)

in which n is an integer from 0 to 10, A denotes a methylene group, optionally linked to the carbon atom of the unsaturated group or to the adjacent methylene group when n is greater than 1 via a hetero atom such as oxygen or sulphur, $R_1$ denotes a hydrogen atom or a phenyl or benzyl group, $R_2$ denotes a hydrogen atom, a lower alkyl group or a carboxyl group, and $R_3$ denotes a hydrogen atom, a lower alkyl group, a —$CH_2COOH$ group or a phenyl or benzyl group.

In the abovementioned formula, a lower alkyl radical preferably denotes a group having 1 to 4 carbon atoms, and in particular methyl and ethyl.

The anionic polymers containing carboxylic groups which are preferred according to the invention are:

A) acrylic or methacrylic acid homo- or copolymers or salts thereof, and in particular the products sold under the names "Versicol E" or "Versicol K" by the company Allied Colloid and "Ultrahold" by the company BASF; the copolymers of acrylic acid and of acrylamide sold in the form of their sodium salt under the names "Reten 421", "Reten 423" or "Reten 425" by the company Hercules; the sodium salts of polyhydroxycarboxylic acids.

B) copolymers of acrylic or methacrylic acids with at least one monoethylenic monomer such as ethylene, styrene, vinyl esters, acrylic or methacrylic acid esters, acrylamide or its derivatives, and vinylpyrrolidone, which are optionally grafted onto a polyalkylene glycol such as polyethylene glycol and optionally crosslinked. Such polymers are described in particular in French patent 1,222,944 and German patent application 2,330,956. The copolymers of this type containing an optionally N-alkylated and/or hydroxy-alkylated acrylamide unit in their chain are described in particular in patents FR 2,360,615 and FR 2,432,528 or are sold under the names "Quadramer" by the company American Cyanamid. Mention may also be made of copolymers of acrylic acid and of ($C_1$–$C_4$)alkyl methacrylate and terpolymers of vinylpyrrolidone, of (meth) acrylic acid and of ($C_1$–$C_{20}$)alkyl (meth)acrylate, for example of lauryl (meth)acrylate, such as the product sold by the company ISP under the name "Acrylidone LM", of tert-butyl (meth)acrylate, for example "Luviflex VBM 70" sold by BASF, or of methyl (meth)acrylate, such as "Stepanhold Extra" sold by Stepan. Mention may also be made of copolymers of methacrylic acid and of ethyl acrylate, such as the product sold under the name "Luvimer MAEX" by the company BASF, and methacrylic acid/ethyl acrylate/tert-butyl acrylate terpolymers such as the product "Luvimer 100P" sold by BASF.

C) Copolymers derived from crotonic acid, such as those containing in their chain vinyl acetate or propionate units and optionally other monomers such as allylic or methallylic esters, vinyl ether or vinyl ester of a linear or branched saturated carboxylic acid with a long hydrocarbon-based chain, such as those containing at least 5 carbon atoms, it being possible for these polymers to be grafted onto a polyalkylene glycol and crosslinked, or alternatively a vinyl, allylic or methallylic ester of an α- or β-cyclic carboxylic acid. Such polymers are described, inter alia, in French patents 1,222,944, 1,580,545, 2,265,782, 2,265,781, 1,564, 110 and 2,439,798. Commercial products forming part of this category are the resins 28-29-30, 26-13-14 and 28-13-10 sold by the company National Starch. Mention may also be made of the vinyl acetate/vinyl p-tert-butylbenzoate/ crotonic acid terpolymer (65/25/10).

D) Copolymers derived from monounsaturated $C_4$–$C_8$ carboxylic acids or anhydrides chosen from:

Copolymers comprising (i) one or more maleic, fumaric or itaconic acids or anhydrides and (ii) at least one monomer chosen from vinyl esters, vinyl ethers, vinyl halides, phenylvinyl derivatives and acrylic acid and its esters, the anhydride functions of these copolymers optionally being monoesterified or monoamidated. Such polymers are described in particular in U.S. Pat. Nos. 2,047,398, 2,723,248 and 2,102,113 and GB patent 839,805 and are sold in particular under the names "Gantrez AN" or "Gantrez ES" or "Avantage CP" by the company ISP.

Copolymers comprising (i) one or more maleic, citraconic or itaconic anhydrides and (ii) at least one monomer chosen from allylic or methallylic esters optionally containing in their chain one or more acrylamide, methacrylamide, α-olefin, acrylic or methacrylic ester, acrylic or methacrylic acid or vinylpyrrolidone groups, the anhydride functions of these copolymers optionally being monoesterified or monoamidated. These polymers are described, for example, in French patents 2,350,384 and 2,357,241 by the Applicant.

E) Polyacrylamides containing carboxylate groups.

The polymers comprising sulphonic groups are polymers containing vinylsulphonic, styrenesulphonic, naphthalenesulphonic or acrylamidoalkylsulphonic units.

These polymers can be chosen in particular from:

Polyvinylsulphonic acid salts having a weight-average molecular weight of between about 1000 and 100,000, as well as their copolymers with an unsaturated comonomer such as acrylic or methacrylic acids and their esters, acrylamide or its derivatives, vinyl ethers and vinylpyrrolidone.

Polystyrenesulphonic acid salts, the sodium salts having a weight-average molecular weight of about 500,000 and of about 100,000 being sold, respectively, under the names "Flexan 500" and "Flexan 130" by National Starch. These compounds are described in patent FR 2,198,719.

Polyacrylamide alkylsulphonic acid salts, such as those mentioned in U.S. Pat. No. 4,128,631 and more particularly polyacrylamidoethylpropanesulphonic acid sold under the name "Cosmedia Polymer HSP 1180" by Henkel and polyacrylamidomethylpropanesulphonic acid crosslinked and partially neutralized to 50% with aqueous ammonia, sold under the name "Hostacerin AMPS" by the company Hoechst.

According to the invention, the anionic polymers are preferably chosen from copolymers of acrylic or methacrylic acid with at least one monoethylenic monomer, which are optionally grafted onto a polyalkylene glycol and optionally crosslinked, such as the acrylic acid/ethyl acrylate/N-tert-butylacrylamide terpolymer sold under the name "Ultrahold Strong" by the company BASF, the copolymers of methacrylic acid and of methyl methacrylate sold under the name "Eudragit L" by the company Rohm Pharma, the copolymer of methacrylic acid and of ethyl acrylate sold under the name "Luvimer MAEX" by the company BASF, the vinylpyrrolidone/acrylic acid/lauryl methacrylate terpolymer sold under the name "Acrylidone LM" by the company ISP, copolymers derived from crotonic acid, such as the vinyl acetate/vinyl tert-butylbenzoate/ crotonic acid terpolymer, the crotonic acid/vinyl acetate/vinyl neododecanoate terpolymer sold under the name "Resin 28-29-30" by the company National Starch, the vinyl acetate/crotonic acid copolymer sold under the name "Luviset CA 66" by the company BASF and the vinyl acetate/crotonic acid/polyethylene glycol terpolymer sold under the name "Aristoflex A" by the company BASF, copolymers derived from maleic, fumaric or itaconic acids or anhydrides, such as the monoesterified methyl vinyl ether/maleic anhydride copolymer sold under the name "Gantrez ES 425" by the company ISP.

The anionic polymers which are most particularly preferred are chosen from vinyl acetate/vinyl tert-butylbenzoate/crotonic acid terpolymer, the monoesterified methyl vinyl ether/maleic anhydride copolymer sold under the name "Gantrez ES 425" by the company ISP, the copolymer of methacrylic acid and of methyl-methacrylate sold under the name "Eudragit L" by the company Rohm Pharma, the copolymer of methacrylic acid and of ethyl acrylate sold under the name "Luvimer MAEX" by the company BASF and the vinylpyrrolidone/acrylic acid/lauryl methacrylate terpolymer sold under the name "Acrylidone LM" by the company IMP.

According to the invention, anionic polymers in latex or pseudolatex form, i.e. in the form of an aqueous dispersion of insoluble polymer particles, can also be used.

It is possible, for example, to use an aqueous dispersion comprising a copolymer formed of one or more alkyl acrylates, of one or more alkyl methacrylates and of one or more ethylenic carboxylic acids having from 3 to 5 carbon atoms, the alkyl radicals having from 1 to 5 carbon atoms and possibly being hydroxylated.

The alkyl acrylate is preferably chosen from methyl acrylate, ethyl acrylate, propyl acrylate and butyl acrylate. Ethyl acrylate is particularly preferred.

The alkyl acrylate concentration is preferably between 40 and 70% by weight and more particularly between 50 and 60% by weight relative to the total weight of the copolymer.

The alkyl methacrylate is preferably chosen from methyl methacrylate, ethyl methacrylate, propyl methacrylate and butyl methacrylate. Methyl methacrylate is particularly preferred.

The alkyl methacrylate concentration is preferably between 30 and 50% by weight and more particularly between 30 and 40% by weight relative to the total weight of the copolymer.

The preferred ethylenic carboxylic acids are acrylic acid, methacrylic acid, crotonic acid and itaconic acid, or mixtures thereof. Acrylic acid and methacrylic acid are particularly preferred. According to the invention, it is possible to use salts of these carboxylic acids.

The concentration of ethylenic carboxylic acids, or salts thereof, is preferably between 5 and 15% by weight and more particularly between 8 and 12% by weight relative to the total weight of the copolymer.

In a particularly preferred embodiment of the invention, acrylic acid is used with methacrylic acid, each in a concentration of between 2 and 10% by weight, the total of these two acids not exceeding 15% by weight of the total weight of the copolymer.

The copolymer can also contain small amounts, i.e. less than 10%, preferably less than 5% and more particularly less than 2%, of a polymerizable monomer other than those mentioned above.

According to a particularly preferred embodiment of the invention, a copolymer comprising from 50 to 60% by weight of ethyl acrylate, from 30 to 40% by weight of methyl methacrylate, from 2 to 10% by weight of acrylic acid and from 2 to 10% by weight of methacrylic acid is used, the total concentration of acrylic and methacrylic acid not exceeding 15% by weight relative to the total weight of the acrylic copolymer.

Such a copolymer is described, for example, in patent BP-A-590,604, which is included herein by way of reference.

An aqueous dispersion of the acrylic copolymer described above comprising 25% by weight of an ethyl acrylate/methyl methacrylate/methacrylic acid/acrylic acid copolymer is sold in particular under the trade name "Amerhold DR-25" by the company Amerchol.

According to the invention, an aqueous dispersion of hydroxyethyl methacrylate/methyl methacrylate/methacrylic acid/butylacrylate copolymer such as, for example, the product sold by the company SEPPIC under the name "Acudyne 255" can also be used.

According to the invention, an aqueous dispersion of ethyl acrylate/methacrylic acid/tert-butyl acrylate copolymer such as, for example, the product sold by the company BASF under the name "Luvimer Low VOC" can also be used.

The anionic polymers are used in the compositions of the invention in proportions of between 0.01 and 20% by weight and preferably between 0.1 and 8% by weight relative to the total weight of the composition.

The compositions according to the invention contain a cosmetically acceptable aqueous medium. They have a pH which can range from 3.5 to 11, preferably between 5.5 and 11 and even more preferably between 5.5 and 8.5.

The cosmetically acceptable medium for the compositions according to the invention consists more particularly of water and optionally of cosmetically acceptable organic solvents.

The organic solvents can represent from 0.5 to 90% of the total weight of the composition. They can be chosen from the group consisting of hydrophilic organic solvents, lipophilic organic solvents, amphiphilic solvents or mixtures thereof.

Among the hydrophilic organic solvents, mention may be made, for example, of linear or branched lower monoalcohols having from 1 to 8 carbon atoms, polyethylene glycols having from 6 to 80 ethylene oxide units, and polyols.

As amphiphilic organic solvents, mention may be made of polypropylene glycol (PPG) derivatives, such as esters of polypropylene glycol and of fatty acid, derivatives of PPG and of fatty alcohol, such as PPG-23 oleyl ether, and PPG-36 oleate.

As lipophilic organic solvents, mention may be made, for example, of fatty esters such as diisopropyl adipate, dioctyl adipate, alkyl benzoates and dioctyl malate.

In order for the cosmetic compositions of the invention to be more pleasant to use (softer when applied, more nourishing and more emollient), it is possible to add a fatty phase to the medium of these compositions.

The fatty phase can represent up to 50% of the total weight of the composition.

This fatty phase can contain an oil or a wax or mixtures thereof, and can also comprise fatty acids, fatty alcohols and fatty acid esters. The oils can be chosen from animal, plant, mineral or synthetic oils and in particular from liquid petroleum jelly, liquid paraffin, isoparaffins, poly-α-olefins, fluoro oils and perfluoro oils. Similarly, the waxes can be chosen from animal, fossil, plant, mineral or synthetic waxes which are known per se.

The compositions of the invention can contain adjuvants that are common in the cosmetics field, such as other standard gelling agents and/or thickeners; emulsifiers; surfactants; moisturizers; emollients; sunscreens; hydrophilic or lipophilic active agents such as ceramides; anti-free-radical agents; sequestering agents; antioxidants; preserving agents; acidifying or basifying agents; fragrances; fillers; dyestuffs; modified or non-modified, volatile or non-volatile silicones; reducing agents. The amounts of these various adjuvants are those used conventionally in the fields considered.

Needless to say, a specialist will take care to select the optional compound(s) to be added to the composition according to the invention such that the advantageous properties intrinsically associated with the composition in accordance with the invention are not, or are not substantially, adversely affected by the addition envisaged.

The compositions according to the invention can be in any form which is suitable for topical application, in particular in the form of a thickened lotion, in the form of aqueous or aqueous-alcoholic gels, in the form of vesicle dispersions or in the form of simple or complex emulsions (O/W, W/O, O/W/O or W/O/W emulsions) and can be of liquid, semi-liquid or solid consistency, such as milks, creams, gels, cream-gels, pastes and sticks, and can optionally be packaged as an aerosol and can be in the form of mousses or sprays. These compositions are prepared according to the usual methods.

The compositions according to the invention are preferably used as rinse-out or leave-in hair products, in particular to wash, dye, care for, condition or straighten the hair, to maintain the hairstyle or to permanently or temporarily reshape the hair.

The compositions can be styling products such as hair-setting lotions, blow-drying lotions, fixing compositions and styling compositions. The lotions can be packaged in various forms, in particular in vaporizers, pump-dispenser bottles or in aerosol containers in order to ensure application of the composition in vaporized form or in the form of a mousse. Such packaging forms are indicated, for example, when it is desired to obtain a spray or a mousse for fixing or treating the hair.

The compositions of the invention can also be shampoos, rinse-out compositions or leave-in compositions, to be applied before or after shampooing, dyeing, bleaching, permanent-waving or straightening the hair.

The compositions of the invention can also be used as hygiene or care products, such as protective, treatment or care creams for the face, for the hands or for the body, protective or care body milks, and skincare or skin cleansing lotions, gels or mousses.

The compositions of the invention can also be used as antisun compositions.

The compositions can also consist of solid preparations constituting cleansing soaps or bars.

The compositions of the invention can also be used as oral care products such as toothpastes and mouthwashes.

The compositions can be make-up products such as face creams, foundations, mascaras, eyeliners, lipsticks or nail varnishes.

Another subject of the invention is a cosmetic, non-therapeutic treatment process for the skin, the scalp, the hair, the eyelashes, the eyebrows, the nails or mucous membranes, characterized in that a composition as defined above is applied to the keratinous support, according to the usual technique for using this composition, for example application of creams, gels, sera, lotions or milks to the skin, the scalp or mucous membranes.

The examples which follow illustrate the invention without being limiting in nature.

EXAMPLE 1

Leave-in Haircare Gel

| | |
|---|---|
| Ethoxylated (40 EO) methacrylic acid/methyl acrylate/behenyl dimethylmetaisopropenyl-benzylisocyanate terpolymer as an aqueous 25% dispersion | 0.5 g AM |
| Vinyl acetate/vinyl p-tert-butylbenzoate/crotonic acid (65/25/10) terpolymer | 0.5 g AM |
| 2-Amino-2-methyl-1-propanol (AMP), qs pH adjusted to 7.5 | |
| Fragrance, preserving agent, dye qs | |
| Demineralized water qs | 100 g |

A thick, clear, non-pasty, non-greasy gel which spreads very well on the hair is obtained. This gel makes the hair feel soft, makes it easy to disentangle and has good fixing power.

If the above terpolymer is replaced by the same amount of "Acrysol 44" polyurethane from Rohm & Haas, a fluid, cloudy gel is obtained.

If the terpolymer is replaced by the crosslinked acrylic acid/$C_{10}$/$C_{30}$ alkyl acrylate copolymer "Pemulen TR1" sold by Goodrich, a slightly pasty gel with very mediocre fixing power and considerably inferior cosmetic properties of softness, feel and ease of disentangling is obtained.

EXAMPLE 2

High-protection Antisun Gel

| | |
|---|---|
| 4-tert-Butyl-4'-methoxydibenzoylmethane ("Parsol 1789" sold by the company Roche) | 2 g |
| Benzene-1,4-di(3-methylidene-10-camphor-sulphonic acid), as an aqueous 33% solution | 3 g |
| 2-Ethylhexyl 2-cyano-3,3-diphenylacrylate ("Uvinul N 539" sold by the company BASF) | 10 g |
| Ethoxylated (40 EO) methacrylic acid/methyl acrylate/behenyl dimethylmetaisopropenylbenzylisocyanate, as an aqueous 25% dispersion | 0.45 g AM |
| Polyacrylamidomethylpropanesulphonic acid crosslinked and partially neutralized to 50% with aqueous ammonia, sold under the name "Hostacerin AMPS" by the company Hoechst | 0.8 g |
| 2,2,4,4,6,6,8-Heptamethylnonane | 9 g |
| Glycerol | 6 g |
| Propylene glycol | 6 g |
| Ethylenediaminetetra (methylenephosphonic acid), pentasodium salt, as an aqueous 33% solution | 0.3 g |
| Triethanolamine | 0.85 g |
| Denatured 96° ethyl alcohol | 4.5 g |
| Sterilized demineralized water qs | 100 g |

A creamy gel which spreads well on the skin is obtained.

What is claimed is:

1. Cosmetic composition for the treatment of keratinous material, comprising, in a cosmetically acceptable aqueous medium, at least one anionic polymer and an acrylic terpolymer comprising:

a) about 20 to 70% by weight, of a carboxylic acid containing α,β-monoethylenic unsaturation;

b) about 20 to 80% by weight, of a non-surfactant monomer containing monoethylenic unsaturation, which is different from a); and c) about 0.5 to 60% by weight, of a nonionic urethane monomer which is the product of reaction of a monohydric nonionic surfactant with a monoisocyanate containing monoethylenic unsaturation.

2. Composition according to claim 1, wherein the carboxylic acid containing α,β-monoethylenic unsaturation a) is acrylic acid, methacrylic acid, itaconic acid or maleic acid.

3. Composition according to claim 2, wherein that the carboxylic acid containing α,β-monoethylenic unsaturation a) is methacrylic acid.

4. Composition according to claim 1 wherein the non-surfactant monomer containing monoethylenic unsaturation b) is $C_1$–$C_4$ alkyl acrylates or methacrylates, styrene, vinyltoluene, vinyl acetate, acrylonitrile or vinylidene chloride.

5. Composition according to claim 4, wherein the non-surfactant monomer containing monoethylenic unsaturation is methyl or ethyl acrylate.

6. Composition according to claim 1 wherein the monohydric nonionic surfactant used to obtain the nonionic urethane monomer c) has the formula:

$$R\text{—}O\text{—}(CH_2\text{—}CH(R')\text{—}O)_m\text{—}(CH_2\text{—}CH_2O)_nH$$

in which R is a $C_6$–$C_{30}$ alkyl or $C_8$–$C_{30}$ aralkyl group, R' is a $C_1$–$C_4$ alkyl group, n is an average number ranging about from 5 to 150 and m is an average number ranging about from 0 to 50, with the condition that n is at least as large as m and that n+m=5–150.

7. Composition according to claim 6, wherein R is a dodecyl, $C_{18}$–$C_{26}$ alkyl or ($C_8$–$C_{13}$) alkylphenyl groups, m=0 and n is an average number ranging from about 5 to 150.

8. Composition according to claim 1 wherein the monoisocyanate containing monoethylenic unsaturation used to form the nonionic urethane monomer c) is α,α-dimethyl-m-isopropenylbenzyl isocyanate.

9. Composition according to claim 1 wherein the acrylic terpolymer is an aqueous dispersion obtained from methacrylic acid as component a), methyl acrylate as component b) and a nonionic urethane macromonomer of the following structure:

$$CH_2\text{=}C(CH_3)\text{—}C_6H_4\text{—}C(CH_3)_2\text{—}NH\text{—}C(=O)\text{—}O\text{—}(CH_2CH_2O)_p\text{—}R^1$$

in which p ranges from 6 to 150 and $R^1$ is a $C_{18}$–$C_{26}$ alkyl radical.

10. Composition according to claim 1 wherein the acrylic terpolymer is present in concentrations ranging from 0.01 to 20% by weight, relative to the total weight of the composition.

11. Composition according to claim 1 wherein the anionic polymers are polymers containing groups derived from carboxylic, sulphonic or phosphoric acid.

12. Composition according to claim 11, wherein the anionic polymers are polymers containing carboxylic groups derived from unsaturated mono- or dicarboxylic acid monomers of formula:

$$R_1R_2C\text{=}CR_3\text{—}(A)_n\text{—}COOH \quad (I)$$

in which n is an integer from 0 to 10, A denotes a methylene group, optionally linked to the carbon atom of the unsaturated group or to the adjacent methylene group when n is greater than 1 via a hetero atom $R_1$ denotes a hydrogen atom or a phenyl or benzyl group, $R_2$ denotes a hydrogen atom, a lower alkyl group or a carboxyl group and $R_3$ denotes a hydrogen atom, a lower alkyl group, a —$CH_2COOH$ group or a phenyl or benzyl group, or polymers comprising vinylsulphonic, styrene-sulphonic, naphthalenesulphonic or acrylamidoalkyl-sulphonic units.

13. Composition according to claim 12, wherein the anionic polymers are:

A) acrylic or methacrylic acid homo- or copolymers or salts thereof, copolymers of acrylic acid or of acrylamide or salts thereof and the sodium salts of polyhydroxycarboxylic acids;

B) copolymers of acrylic or methacrylic acids with at least one monoethylenic monomer chosen from ethylene, styrene, vinyl esters, acrylic or methacrylic acid esters, acrylamide or its derivatives or vinyl-pyrrolidone, which are optionally grafted onto a polyalkylene glycol and optionally crosslinked;

C) copolymers derived from crotonic acid containing in their chain vinyl acetate or propionate units and optionally other monomers chosen from allylic or methallylic esters, vinyl ether or vinyl ester of a linear or branched saturated carboxylic acid with a long hydrocarbon-based chain containing at least 5 carbon atoms, or a vinyl, allylic or methallylic ester of an α- or β-cyclic carboxylic acid, it being possible for these polymers to be optionally grafted onto a polyalkylene glycol and crosslinked;

D) copolymers derived from monounsaturated $C_4$–$C_8$ carboxylic acids or anhydrides chosen from copolymers comprising (i) one or more maleic, fumaric or itaconic acids or anhydrides or (ii) at least one monomer chosen from vinyl esters, vinyl ethers, vinyl halides, phenylvinyl derivatives or acrylic acid and its esters, the anhydride functions of these copolymers optionally being monoesterified or monoamidated or copolymers comprising (i) one or more maleic, citraconic or itaconic anhydrides and (ii) one or more monomers chosen from allylic or methallylic esters optionally containing in their chain one or more acrylamide, methacrylamide, α-olefin, acrylic or methacrylic ester, acrylic or methacrylic acid or vinylpyrrolidone groups, the anhydride functions optionally being monoesterified or monoamidated; or E) polyacrylamides containing carboxylate groups.

14. Composition according to claim 13, wherein the anionic polymers are copolymers of methacrylic acid or of methyl methacrylate, copolymers of methacrylic acid and of ethyl acrylate, vinylpyrrolidone/acrylic acid/lauryl methacrylate terpolymers, methacrylic acid/ethyl acrylate/tert-butyl acrylate terpolymers, acrylic acid/ethyl acrylate/N-tert-butylacrylamide terpolymers, vinyl acetate/crotonic acid copolymers, vinyl acetate/vinyl tert-butylbenzoate/crotonic acid terpolymers, crotonic acid/vinyl acetate/vinyl neododecanoate terpolymers, vinyl acetate/crotonic acid/polyethylene glycol terpolymers and monoesterified methyl vinyl ether/maleic anhydride copolymers.

15. Composition according to claim 14, wherein the anionic polymers are vinyl acetate/vinyl tert-butylbenzoate/crotonic acid terpolymers, monoesterified methyl vinyl ether/maleic anhydride copolymers, copolymers of methacrylic acid and of methyl methacrylate, copolymers of methacrylic acid or of ethyl acrylate and vinylpyrrolidone/acrylic acid/lauryl methacrylate terpolymers.

16. Composition according to claim 12, wherein the anionic polymers are:

polyvinylsulphonic acid salts having a weight-average molecular weight of between about 1000 or 100,000 and copolymers thereof with acrylic or methacrylic acids or their esters, acrylamide or its derivatives, vinyl ethers or vinylpyrrolidone;

polystyrenesulphonic acid salts or;

polyacrylamidealkylsulphonic acid salts.

17. Composition according to claim 16, wherein the anionic polymers comprising sulphonic groups are polyacrylamidoethylpropanesulphonic acid or polyacrylamidomethylpropanesulphonic acid crosslinked or partially neutralized to 50% with aqueous ammonia.

18. Composition according to claim 1 wherein the anionic polymers are in the form of an aqueous dispersion of insoluble particles of anionic polymers chosen from copolymers formed of one or more alkyl acrylates, of one or more alkyl methacrylates or of one or more ethylenic carboxylic acids having from 3 to 5 carbon atoms, the alkyl radicals having from 1 to 5 carbon atoms and optionally being hydroxylated.

19. Composition according to claim 18, wherein the aqueous dispersion of insoluble particles of anionic polymers comprises an ethyl acrylate/methyl methacrylate/methacrylic acid/acrylic acid copolymer, a hydroxyethyl methacrylate/methyl methacrylate/methacrylic acid/butyl acrylate copolymer or an ethyl acrylate/methacrylic acid/tert-butyl acrylate copolymer.

20. Composition according to claim 1 wherein the anionic polymers are present in concentrations ranging from 0.01 to 20% by weight, relative to the total weight of the composition.

21. Composition according to claim 1 wherein the composition it has a pH ranging from 3.5 to 11.

22. Composition according to claim 1 wherein the cosmetically acceptable aqueous medium consists of water or of water and at least one organic solvent selected from the group consisting of hydrophilic, lipophilic and amphiphilic organic solvents and mixtures thereof.

23. Composition according to claim 1, further comprising at least one fatty substance, gelling agent and/or thickener, surfactant, moisturizer, emollient, sunscreen, hydrophilic or lipophilic active agent, anti-free-radical agent, sequestering agent, antioxidant, preserving agent, acidifying or basifying agent, fragrance, filler, dyestuff, silicone or reducing agent.

24. Composition according to claim 1 wherein the composition it is in the form of an emulsion, a thickened lotion, a gel, a vesicle dispersion, a paste or a solid stick or is packaged as an aerosol and is in the form of a mousse or a spray.

25. Composition according to claim 1 wherein the composition it is a rinse-out or leave-in hair product to wash, dye, care for, condition or straighten the hair, to maintain the hairstyle or to permanently or temporarily reshape the hair, or as an antisun composition.

26. Cosmetic, non-therapeutic treatment process for treating keratinous material comprising applying an effective amount of a composition as defined in claim 1 to the keratinous material.

27. Composition according to claim 1, wherein the acrylic terpolymer comprises about 25 to 55% by weight of the carboxylic acid containing α,β-monoethylenic unsaturation, about 30 to 65% by weight of the non-surfactant monomer containing monoethylenic unsaturation and about 10 to 50% by weight of the nonionic urethane monomer.

28. Composition according to claim 9, wherein $R^1$ is a linear $C_{20}$–$C_{24}$ alkyl radical of plant origin.

29. Composition according to claim 28, wherein the alkyl radical of plant origin is the docosyl radical.

30. Composition according to claim 10, wherein the concentration of acrylic terpolymer is from 0.1 to 10% by weight.

31. Composition according to claim 20, wherein the concentration of anionic polymer is from 0.1 to 8% by weight.

32. Composition according to claim 21, wherein the pH range is from 5.5 to 8.5.

33. Process according to claim 26, wherein the keratinous material is skin, scalp, hair, eyelashes, eyebrows, nails or muscous membranes.

* * * * *